United States Patent [19]

Nagy et al.

[11] 4,026,145
[45] May 31, 1977

[54] HYDRAULIC GRIP FOR TUBULAR MECHANICAL PROPERTIES SPECIMEN

[75] Inventors: Andrew Nagy; Ulric S. Lindholm; Lester M. Yeakley, all of San Antonio, Tex.

[73] Assignee: The United States of America as represented by the Secretary of the Air Force, Washington, D.C.

[22] Filed: Apr. 16, 1976

[21] Appl. No.: 677,591

[52] U.S. Cl. ................................................. 73/103
[51] Int. Cl.² ......................................... G01N 3/04
[58] Field of Search ................. 73/103, 99, 93, 94, 73/95, 49.5, 49.6; 214/1 P

[56] References Cited
UNITED STATES PATENTS 2,920,895  1/1960  Krouse .................................. 73/103
3,662,591  5/1972  Bons .................................... 73/103

*Primary Examiner*—James J. Gill
*Assistant Examiner*—Anthony V. Ciarlante
*Attorney, Agent, or Firm*—Joseph E. Rusz; Arsen Tashjian

[57] ABSTRACT

A hydraulically actuated collet type grip with an elastic support structure to allow for the axial bending needed to compensate for diametral dimension changes in the specimen gage section to be accomodated within the grip rather than within the tubular specimen. The tabbed end of the tubular specimen is gripped in the annular region of the loud transfer section of the collet. Load transfer is achieved by normal pressure on the collet and the frictional interface between the collet and the bonded end tabs on the specimen.

4 Claims, 3 Drawing Figures

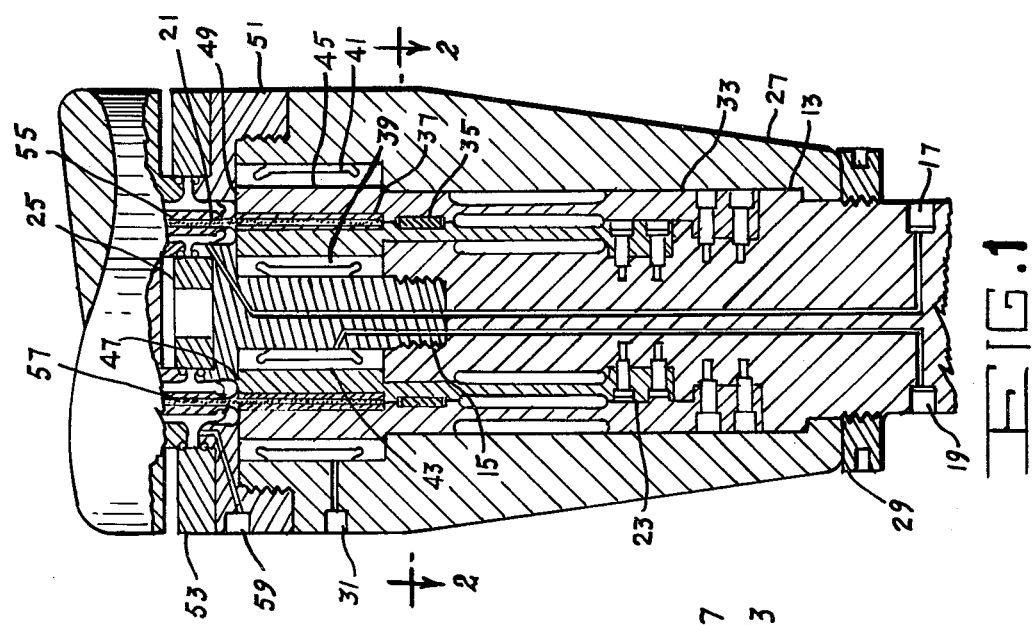
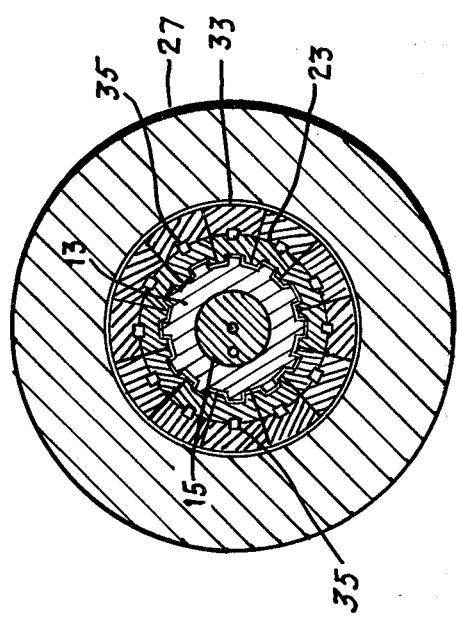
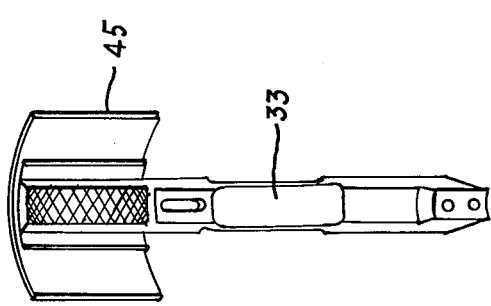

HYDRAULIC GRIP FOR TUBULAR MECHANICAL PROPERTIES SPECIMEN

STATEMENT OF GOVERNMENT INTEREST

The invention described herein may be manufactured and used by or for the Government for governmental purposes without the payment of any royalty thereon.

BACKGROUND OF THE INVENTION

This invention relates to a hydraulic grip for tubular mechanical properties specimens and, more particularly, the invention is concerned with providing a grip which is capable of applying in-place loads, singly and in combination, with minimum constraint to tubular specimens.

The tubular specimen for mechanical property determinations has been used successfully for many years in the study of metal plasticity. The state of generalized plane stress can be achieved by the independent application of axial loads, internal or external surface pressure, and torque about the longitudinal axis of the tube. For metals, the specimen may have a reduced wall thickness gage section and be rigidly attached through the thicker end tab section to the testing machine. Stress concentrations introduced by the change in section and rigid grip are relieved by local plastic flow. However, for brittle materials, such as ceramics, rocks and many high strength composites, the stress concentrations at the grip boundaries become critical and cause premature failure of the specimen during test. As yet, a completely satisfactory solution has not been found to the problem of multiaxial strength testing of brittle materials, particularly when all components of a plane stress condition are required.

The following general problems are encountered during the multiaxial strength testing of brittle materials:

1. If load tabs or change in section thickness are used, the change in specimen compliance results in local extraneous or nonhomogeneous stresses during load application.
2. If load tabs are used, functional or material failure in the tab or the adhesive bond must be avoided.
3. High surface pressures on the tube gage section used to produce in-plane circumferential or axial load components may produce states of stress that are no longer biaxial.
4. Thin-walled tubular specimens must be designed to undergo material failure before the onset of structural failure, buckling, under compressive load.
5. The cost of meaningful multiaxial testing in terms of equipment, specimen fabrication and test procedure, may become excessive.

An ideal solution to the above-mentioned problems would include a grip design which is capable of applying, with minimum constraint, in-place loads, singly and in any combination, to tubular specimens. The loads should be capable of being applied under static and low cycle fatigue conditions at different rates and at different temperatures.

SUMMARY OF THE INVENTION

The present invention is concerned with providing an improved grip for introducing loads into a tubular specimen. The multi-axial load introduction is achieved in such a manner that the boundary constraint on the load induced deformation of the tube is reduced to a level at which it plays no significant role in either the deformation or failure mode of the free gage section of the tube. This is necessary in order that the measured applied loads may be uniquely correlated with a uniform stress distribution within a defined volume of the specimen and that failure will occur within this defined volume. In particular, for accurate failure strength determination, it is necessary that the principal stress components have their maximum values within the defined volume or gage section of the specimen. End constraint which prevents radial displacement or rotation leads to the development of stress states near the boundary that are more severe than at the center of the specimen, leading to potential premature failure. The present grip design reduces these boundary constraints to an acceptable level.

Accordingly, it is an object of the invention to provide a grip for applying loads to tubular specimens of brittle material such that no local extraneous or nonhomogeneous stresses are applied because of the load tabs or change in section thickness.

Another object of the invention is to provide a hydraulically actuated collet type grip for use with brittle tubular specimens wherein functional or material failure of the tab and/or adhesive bond is avoided where load tabs are used.

Still another object of the invention is to provide a grip for use with tubular specimens for mechanical property determinations wherein there high surface pressures on the tube gage section used to produce in-plane circumferential or axial load components produce states of stress that are biaxial.

A further object of the invention is to provide a specimen grip design which is capable of applying inplane loads, singly and in combination with minimum constraint to tubular specimens.

A still further object of the invention is to provide a hydraulically actuated collet type grip with an elastic support structure. The elastic support allows for radial displacement needed to compensate for diametral dimension changes in the specimen gage section.

These and other objects, features, and advantages will become more apparent after considering the following detailed description taken in conjunction with the annexed drawings and appended claims.

BRIEF DESCRIPTION OF THE DRAWINGS

FIG. 1 is a longitudinal cross-sectional view of the lower grip according to the invention showing the tubular specimen in position with the tabbed end gripped between the inner and outer collets;

FIG. 2 is a view of the grip taken along the line 2—2 of FIG. 1 showing the lower portions of the segments of the inner and outer collets attached to the grip stem; and FIG. 3 is a view in front elevation of one of the outer collet segments with backup plates according to the invention.

DESCRIPTION OF A PREFERRED EMBODIMENT

Referring now to the drawing wherein like reference characters designate identical parts throughout the views, in FIG. 1 there is shown a longitudinal cross-sectional view of the lower grip, the upper grip being substantially identical thereto except for one detail of pressure porting. The stem 13 is connected by means of a bolted flange connection (not shown) to either a biaxial load cell for the upper grip or to the shaft of a linear hydraulic actuator for the lower grip. The stem 13 and the stem extension 15 contain the pressure ports 17 and 19 for the internal pressurization of the specimen 21 and pressure for the inner collet 23, respectively. In the matching grip, the specimen internal pressurization port is replaced by a venting port to the center of the internal pressurization seal ring 25.

The housing 27 is secured in position by the housing locking ring 29. The housing 27 is a cylindrical thick shell which serves as pressure containment for the collet. The pressure port 31 for the outer collet is contained in the housing 27.

The axial and torsional components of the applied loading are transferred from the stem 13 into the specimen 21 through the outer collet segments 33 and the inner collet segments 23. Preferably, there are twelve matched pairs (inner and outer) of these collet segments in the circumferential direction. Each pair is keyed together with a torsional transfer key 35. This key 35 locks the segments together torsionally, so that if gross slippage occurs between one collet and the specimen, as could be caused by loss in collet pressure, all the torsional load is not transferred onto one collet. The key 35 is basically an overload protection device.

The tabbed end 37 of the tubular specimen 21 is gripped in the annular region of the load transfer section of the collet. Load transfer is achieved by normal pressure on the collet and the frictional interface between the collet and the bonded end tabs 37 on the specimen 21. The contact surface of the collet may be knurled as in the typical segment shown in FIG. 3. The normal gripping pressure is achieved in the inner pressure annulus between the stem extension 15 and the inner collet 23 and in the annulus between the outer collet 33 and the housing 13. These pressure chambers are sealed by means of the elastomeric inner collet seal 39 and elastomeric outer collet seal 41, the inner vertical liner 43 and the outer vertical liner 45, and the inner horizontal liner 47 and the outer horizontal liner 49. The collet seals 39 and 41 are continuous, cylindrical, spring loaded, elastomeric, pressure activated, positive seals. The vertical and horizontal liners 41, 43, 45 and 47 are thin segmented sections of sheet material which effectively prevent pressure extrusion of the elastomeric seal material between the gaps in the segmented collets. This is a variable gap produced by expansion or contraction of the collet during deformation of the specimen 21. The outer gland cap 51 completes the containment of the grip pressurization system. The vertical liners 43 and 45 support the elastomeric seals 39 and 41 over a length which remains constant, therefore additional corner seals are not required. Vertical clearance between the ends of the load transfer section of the collets and the outer gland cap 51 and shoulder on the housing 27 is provided to take up axial displacement and rotation caused by strain in the elastic portions of the collet segments. These displacements are accomodated by slip between the collets and the liners.

Pressurization chambers for internal and external pressurization of the specimen gage length between the grips are completed by means of the internal pressurization seal ring 25 and external pressurization seal ring 53, respectively. These two rings are free floating in the axial direction in order to allow free axial crosshead displacement. Radially, they are sealed with respect to the moving upper and lower grips by the "O" ring seals as shown. The length of these pressure seal rings 25 and 53 must be matched to the specimen gage length. Different pairs of rings would be required for each significant change in specimen gage length. Spring-loaded seals 55 and 57 are usd to seal the specimen surface from the hydraulic pressurizing fluid. These elastomer seals are backed up by the metal corner seals preventing extrusion at the intersection of the horizontal collet liners 47 and 49 and the stem extension 15 or gland cap 51. These metal seals are constant diameter. Pressure porting for the external specimen chamber 59 is contained in the outer gland cap 51.

Each collet segment is basically a cantilever beam, fixed at its root to the stem 13 of the grip by two 0.250-inch diameter bolts. Axial loads are carried by the overlapping shoulder on the stem 13. Each segment then has a reduced thickness section where beam flexure is allowed to occur. This is the elastic section of the collet which provides for radial and torsional compliance. The remainder of the collet segment is the pressurized load transfer section.

Radial displacement of the collet is limited by the clearance between the inner collet and the stem and between the outer collet and the housing. In both cases this clearance is 0.0375 inch or an allowable maximum circumferential strain in the specimen of 2%. Tensile or compressive failure strains for most brittle materials will be within this limit. This deflection limit is also a controlling factor on the dimensions of the elastic segments, controlling the root stresses due to bending. These stresses are designed to be within the fatigue endurance limit of 125,000 psi for the material used to fabricate the collet. Torsional displacement of the collet is limited by the clearance in the keyed segment 35 between the inner collet 23 and the stem 13. These clearances are governed again by the allowable torsional bending stress at the root of the collet. Using conservative estimates, the collet can support 25,000 in-lbs of torque elastically before seating on the positive torsional stops. For torque greater than this amount, the excess torque is carried by the stem 13.

The axial clearance between the ends of the collet segments and the stem 13 and outer housing 27 is governed by the collet rotation due to axial and torsional bending and to axial strain in the collet. The total displacement due to these sources is a maximum of 0.020 inch. The circumferential clearance required between collet segments is based on the maximum 2% circumferential strain. For twelve collet segments, the required clearance is 0.0186 inch.

Appropriate setting of these axial, rotational and radial displacement limits prevents the machine from overloading the elastic elements of the collet. The load limits for the grip as designed are:

| | |
|---|---|
| Compression | 166,930 lbs |
| Tension | 112,880 lbs |
| Torsion | 123,200 in-lbs |

These loads are based upon the fatigue endurance limit. The static yield limit is greater than 2.5 times the endurance limit. The fatigue design loads for the grip will allow testing of 0.060-inch wall thickness, 3.750-inch outside diameter tube at an alternating axial stress of 240,00 psi.

The specimen is designed for a relatively thin bonded end tab. The design spacing between collet faces is 0.260 inch. For a normal specimen wall thickness of $t =$ 0.60 inch, the inner and outer tab thickness is 0.10 inch. In general, the thickness of the tab will vary with specimen thickness in order to yield the constant total thickness of 0.260 inch. The length of the tabbed load transfer section is 3.0 inches. The materials used for tab construction may vary, depending upon the specimen laminate construction, applied load ratio and maximum load transfer requirement. The construction could range from cast pure epoxy, glass cloth reinforced epoxy, or unidirectional E glass/epoxy tabs. The tab construction can play an important role in controlling the boundary constraint stresses. Considerable flexibility in tab design can be considered within the fixed design parameters of the hydraulic grip. The tabs function to dissipate the normal contact stresses between the serrated collet and the speciment and provide a good frictional load transfer surface. Also, the tab is needed to dissipate, by means of shear deformation, the different in in-plane strain between the essentially rigid collet segments and the deforming specimen. The thickness and shear stiffness of the tab material are important in this regard.

Although the invention has been illustrated in the accompanying drawings and described in the foregoing specification in terms of a preferred embodiment thereof, the invention is not limited to this embodiment or to the particular configuration disclosed. It will be apparent to those skilled in the art that certain changes, modifications and substitutions can be made, particularly with respect to the construction details, without departing from the true spirit and scope of the appended claims.

Having thus set forth the nature of my invention, what we claim and desire to secure by Letters Patent of the U.S. is:

1. A hydraulic grip for holding and transmitting multiaxial loads with minimum constraint from a testing machine to a brittle tubular test specimen, said grip comprising a round elongated vertically oriented stem member for operative attachment to the testing machine, a thick walled cylindrical housing positioned around said stem member, the upper portion of said housing being spaced radially away from said stem member, a locking ring threadably positioned around said stem member against the lowermost end of said housing for securing said housing to said stem member, and hydraulically actuated gripping means positioned between said housing and said stem member for holding the tubular test specimen while applying multiaxial loads such that the boundary constraint on the load induced deformation of the tubular specimen is reduced to a minimum level thereby playing no significant role in the deformation and failure mode of the free gage section of the specimen.

2. The hydraulic grip defined in claim 1 wherein the gripping means for holding the tubular test specimen while applying multiaxial loads thereto includes an inner collet having its lower end fixedly attached to said stem member, the upper end of said inner collet being positioned between the specimen and the upper portion of said stem member, an outer collet fixedly attached to the said stem member, the upper end of said outer collet being positioned between the specimen and said housing, and hydraulically actuated means for urging said inner collet outward and said outer collet inward causing said test specimen to be held therebetween during the application of loads thereto.

3. The hydraulic grip defined in claim 2 wherein said inner and outer collets are longitudinally segmented, the lower end of each longitudinal segment of said inner collet being separately affixed to said stem member and the lower end of the longitudinal segment of said outer collet being separately affixed to said stem member below said inner collet segments, and a torsional transfer key positioned between each pair of inner and outer collet segments thereby locking the segments together torsionally.

4. The hydraulic grip defined in claim 2 wherein the hydraulically actuated means for urging said inner collet outward and said outer collet inward includes a collet internal pressure port in the lower end of said stem member, an elastomeric inner seal positioned between the inner wall of the inner collet and the stem member, said collet internal pressure port being in operative communication with said elastomeric inner seal, a collet outer pressure port in the wall of said housing, and an elastomeric outer seal positioned between the outer wall of the outer collet and the housing, said collet outer pressure port being in operative communication with said elastomeric outer seal.

* * * * *